(12) United States Patent
Jalenques

(10) Patent No.: US 9,914,903 B2
(45) Date of Patent: Mar. 13, 2018

(54) AUTOMATIC DEVICE AND METHOD FOR INOCULATING A SAMPLE AT DIFFERENT CONCENTRATIONS

(75) Inventor: M. Emmanuel Jalenques, St Nom la Breteche (FR)

(73) Assignee: INTERLAB, St Nom la Bretêche (FR)

( * ) Notice: Subject to any disclaimer, the term of this patent is extended or adjusted under 35 U.S.C. 154(b) by 554 days.

(21) Appl. No.: 13/614,438

(22) Filed: Sep. 13, 2012

(65) Prior Publication Data

US 2013/0065268 A1    Mar. 14, 2013

(30) Foreign Application Priority Data

Sep. 14, 2011  (FR) ...................................... 11 58198

(51) Int. Cl.
*C12M 1/26*        (2006.01)

(52) U.S. Cl.
CPC ................................... *C12M 33/00* (2013.01)

(58) Field of Classification Search
CPC ....................................................... C12M 33/00
See application file for complete search history.

(56) References Cited

U.S. PATENT DOCUMENTS

| 5,104,621 | A | * | 4/1992 | Pfost et al. ...................... 422/67 |
| 6,901,819 | B2 | * | 6/2005 | Gilson ................... G01N 35/10 |
|  |  |  |  | 73/864.25 |
| 8,691,558 | B2 | * | 4/2014 | Gupta et al. ................ 435/286.3 |
| 2006/0210435 | A1 | * | 9/2006 | Alavie ................. G01N 21/253 |
|  |  |  |  | 422/65 |
| 2009/0220385 | A1 | * | 9/2009 | Brown ................ B01F 13/1055 |
|  |  |  |  | 422/400 |

* cited by examiner

*Primary Examiner* — Lisa J Hobbs
(74) *Attorney, Agent, or Firm* — Thomas P. O'Connell; O'Connell Law Firm

(57) ABSTRACT

An automatic device for inoculating a sample on a substrate with a dilution mechanism formed by a head that holds a stylus in cooperation with a first dilution tank and a second dilution tank to dilute an original sample in at least one sub-sample and for inoculating the sub-sample on a substrate.

20 Claims, 1 Drawing Sheet

AUTOMATIC DEVICE AND METHOD FOR INOCULATING A SAMPLE AT DIFFERENT CONCENTRATIONS

FIELD OF THE INVENTION

The present invention relates to the field of the automatic devices for inoculating a culture substrate with a sample to be analyzed, usually a substantially liquid sample. It relates more particularly to a system to take and inoculate the sample, for example on a substrate in a Petri dish.

BACKGROUND OF THE INVENTION

In an automatic inoculating device, each sample is taken from a sample tank by the automatic device using a stylus and is then distributed on the substrate surface using the same stylus.

The stylus must be moved from one area of sample collection in the corresponding tank to an inoculating area in which the sample must be distributed, generally in a spiral pattern. The spiral pattern enables to obtain a variable concentration of the sample along the pattern.

However, the reading and interpretation of the culture results are generally difficult. Moreover, differences in concentration between the most extreme areas are not always sufficient, in particular when the sample is highly concentrated.

SUMMARY OF THE INVENTION

In view of the foregoing, the invention disclosed herein proposes an automatic device that overcomes the above-mentioned inconveniences. More particularly, the present invention seeks to provide an automatic device that is elegant and efficient in construction thereby reducing manufacturing and other costs while being capable of carrying out an easy and efficient manipulation of a sample and, simultaneously, a simple and accurate reading of the results.

These and in all likelihood further objects and advantages of the present invention will become obvious not only to one who reviews the present specification and drawings but also to those who have an opportunity to experience an embodiment of the automatic device disclosed herein. Although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In certain embodiments, the invention proposes achieving at least one of the abovementioned purposes through an automatic device for inoculating a sample on a substrate that comprises means for diluting an original sample in at least one sub-sample and means for inoculating the at least one sub-sample on a substrate. Embodiments of the invention can have dilution means that perform at least two successive dilutions.

The dilution means can take the form of at least one tank for the original sample and at least one tank, preferably at least two tanks, where a sample can be mixed with diluents. The original sample container can, for example, be a tank, a pipet, a syringe, a stylus, or any other sample container that might now exist or hereafter be developed.

The automatic device can comprise adapted means for collecting a sample in its respective tank and for distributing the sample on a substrate, storing means for storing the diluents, and measurement means for measuring the sample and diluents.

The taking or collecting means can be a stylus or a syringe. When the collecting means takes the form of a stylus, means for supplying diluents from upstream of the stylus can be provided.

The invention relates also to an inoculation process of a Petri dish using an automatic device according to the invention.

One will appreciate that the foregoing discussion broadly outlines the more important goals and features of the invention to enable a better understanding of the detailed description that follows and to instill a better appreciation of the inventor's contribution to the art. Before any particular embodiment or aspect thereof is explained in detail, it must be made clear that the following details of construction and illustrations of inventive concepts are mere examples of the many possible manifestations of the invention.

BRIEF DESCRIPTION OF DRAWINGS

Several embodiments and execution modes of the invention will be described below, as non-limited examples, with references to the accompanying drawings, in which.

In the figures and in the remainder of the description, the components common to the figures retain the same reference number.

DETAILED DESCRIPTION OF PREFERRED EMBODIMENTS

Figure 1:
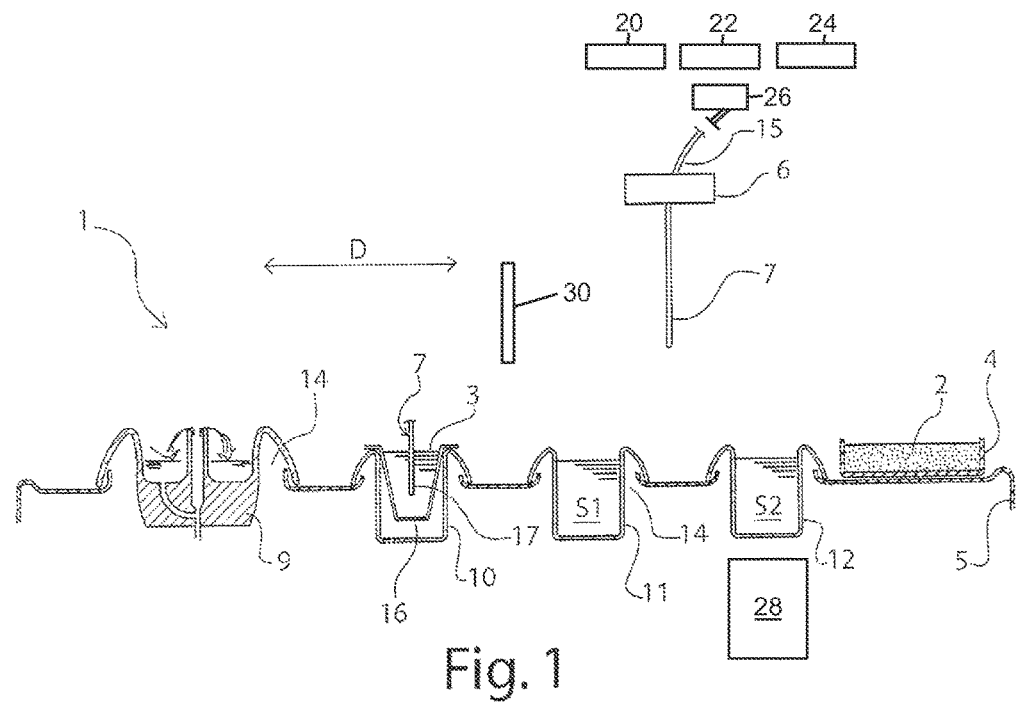
FIG. 1 is a sectional, schematic view of an inoculating device according to the invention in operation.

The automatic device for inoculating a sample at different concentrations and the method for using the same for sample inoculation disclosed herein are subject to widely varied embodiments. However, to ensure that one skilled in the art will be able to understand and, in appropriate cases, practice the present invention, certain preferred embodiments of the broader invention revealed herein are described below and shown in the drawings. Before any particular embodiment of the invention is explained in detail, it must be made clear that the following details of construction and illustrations of inventive concepts are mere examples of the many possible manifestations of the invention.

Turning more particularly to the drawings, an automatic device for inoculating a substrate 2 with a sample 3 of a product to be analysed is indicated generally at 1 in FIG. 1. In the illustrated example, the substrate 2 is contained in a Petri dish 4. The substrate 2 can take the form of a gel, and the sample 3 of the product is substantially liquid.

The automatic device 1 includes a frame with a platform 5 and a head 6 movable above the platform 5. The head 6 holds a stylus 7 that handles the sample 3.

The automatic device 1 also has several removable tanks 9, 10, 11, and 12 placed in respective openings 14 in the platform 5, thereby permitting a positioning of the tanks 9, 10, 11, and 12.

One of the tanks is what can be referred to as a cleaning tank 9 for cleaning the stylus 7. In the illustrated example, the cleaning tank 9 is a pour tank. Another tank 10 is a tank for storing the original sample 3, and the other two tanks 11 and 12 comprise a first dilution tank 11 and a second dilution tank 12.

In the illustrated example of the automatic device 1 of FIG. 1, the tanks 9, 10, 11, and 12 are disposed in line with one another and in line with the Petri dish 4. The head 6 includes means for moving the head 6 and the retained stylus 7 in translation along three axes, namely two horizontal axes and the vertical axis.

Figure 2:
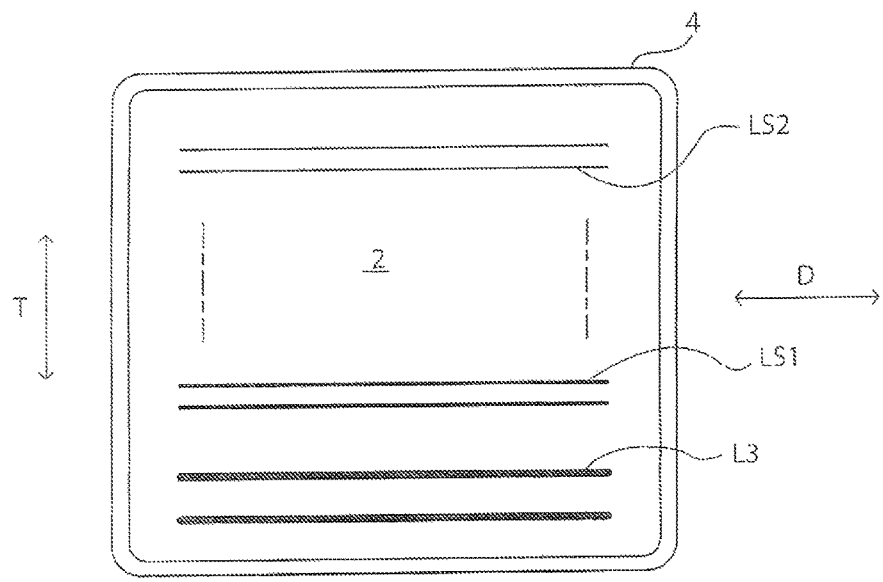
FIG. 2 is a top plan view of a Petri dish where a sample has been inoculated pursuant to the method and device taught herein.

Looking additionally to FIG. 2, the head 6 and the retained stylus 7 under this construction can move horizontally from one tank 9, 10, 11, or 12 to another in a direction parallel to the alignment direction D of the tanks 9, 10, 11, or 12. The head 6 and stylus 7 can dip vertically and move transversally and horizontally according to the horizontal and transversal directions D and T.

The stylus 7 can be formed by a tube. The stylus 7 is connected upstream to a pipe 15 as illustrated in FIG. 1. Upstream of the pipe 15, the automatic device 1 comprises a storage area 20 for a cleaning product and a storage area 22 for a disinfecting product to clean and disinfect the stylus 7 between two takings and/or between two dilutions, a storage area 24 for a diluents product for dilution of the sample 3, and a pump 26 acting as means for taking and inoculating the sample 3 and distributing the products from their respective storage areas 20, 22, and 24. The automatic device 1 also includes means for mixing the samples in the dilution tanks. That means can comprise, for example, an electromagnetic agitator 28.

In FIG. 1, the sample 3 is contained in a beaker 16 that is placed inside the sample tank 10. An extremity 17 of the stylus 7 is represented in a taking position of the sample 3.

The automatic device 1 can be employed to carry out an inoculating method according to the invention. By use of the automatic inoculating device 1, a dilution can be effected through which one can, among other things, count the number of bacteria present by unit of volume in a sample 3.

With combined reference to FIGS. 1 and 2, it is possible in the illustrated example to collect a sample 3 in the beaker 16 and then to distribute a portion of the sample 3 on the substrate 2 to draw a double line L3. Then, another portion of the sample 3 can be mixed in the first dilution tank 11 with diluents retained therein, for example in a $1/10$ proportion. Once the sample 3 is so mixed with the diluents, a first sub-sample S1 is obtained that can be inoculated under a double line LS1.

The same operation is then carried out with sub-sample S1. More particularly, a portion of the first sub-sample S1 is mixed in the second dilution tank 12 with diluents, for example in a $1/10$ proportion. Once the sub-sample S1 is so mixed with the diluents, a second sub-sample S2 is obtained that represents a $1/100e$ dilution of the original sample 3. This second sub-sample S2 can be inoculated under a double line LS2. If desired, the same operation can be repeated after the first dilution tank 11 is replaced by a third one (not shown) and so on.

The above-described operations are automatically executed by the automatic device 1. Such operations can advantageously be programmable, including in relation to the particular successive dilution rates and the number of lines L3, LS1, and LS2.

When the lines L3, LS1, and LS2 are all drawn at a same linear speed, the same line length always represents the same sample quantity, provided that the dilution rate is the same. As a result, it is very easy to measure the result with a measurement device 30 for measuring the sample 3 and the first and second sub-samples S1 and S2 as disposed in the lines L3, LS1, and LS2 and to analyze the results without error and without a need for sophisticated charts and the like to permit an interpretation of the results.

Of course, the invention is not limited to the examples described hereinabove. For instance, instead of being removable, the cleaning or pour tank 9 and/or one or more other tanks 10, 11, and 12 can be fixed in place, such as by being directly shaped as by stamping into the platform 5 of the automatic device 1. Also, the cleaning tank 9 can be another system than a pour tank. Still further, instead of being mounted in translation, the head 6 can be mounted on an arm hanging from a rotating turret (not shown). In such embodiments, the tank positions can be different; for instance the tanks 9, 10, 11, and 12 can be positioned along a circle. The number of dilution tanks 11 and 12 can also vary; only one dilution tank can be employed, or there can be more than two. In particular, when there are several dilution tanks, determined dilution rates can only be inoculated, the others being intermediary dilutions aiming to obtain the desired dilution rate. Even further, rather than linear patterns for the lines L3, LS1, and LS2, patterns being points with more or less thickness or circular patterns can also be planned.

Of course the invention is not limited to the examples which have just been described. Indeed, with certain details and embodiments of method and device of the present invention disclosed, it will be appreciated by one skilled in the art that changes and additions could be made thereto without deviating from the spirit or scope of the invention. This is particularly true when one bears in mind that the presently preferred embodiments merely exemplify the broader invention revealed herein. Accordingly, it will be clear that those with certain major features of the invention in mind could craft embodiments that incorporate those major features while not incorporating all of the features included in the preferred embodiments.

Therefore, the following claims are intended to define the scope of protection to be afforded to the inventor. Those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, these claims shall be construed to cover not only the corresponding structure and material expressly described in this specification but also all equivalents thereof that might be now known or hereafter discovered.

I claim as deserving the protection of Letters Patent:

1. An automatic device for inoculating an original sample on at least one substrate contained in at least one Petri dish, the automatic device comprising:
   a cleaning tank;
   at least one storage area for retaining the original sample;
   at least one dilution tank;
   a stylus comprising a tube adapted to take the original sample from the at least one storage area, to distribute the original sample on the at least one substrate contained in the at least one Petri dish, to dilute a portion of the sample with diluent in the at least one dilution tank to create at least a first sub-sample, to take at least a portion of the first sub-sample, and to distribute the at least a portion of the first sub-sample on the at least one substrate contained in the at least one Petri dish;

a platform that retains the at least one storage area for the original sample, the cleaning tank, the at least one dilution tank, and the at least one substrate contained in the at least one Petri dish;

a head wherein the head is movable horizontally relative to the platform, wherein the head is movable vertically relative to the platform, and wherein the head retains the stylus;

a storage area for diluent disposed upstream of the stylus for supplying diluent to the stylus;

a storage area for disinfecting product disposed upstream of the stylus for supplying disinfecting product to the stylus; and a pump connected to the tube of the stylus to permit taking and distribution of liquids from the at least one storage area for the original sample, the at least one dilution tank, and the storage areas for diluent and the disinfecting products;

wherein, by programmed operation of the head and the pump, the automatic device automatically takes at least a portion of the original sample from the least one storage area for the original sample through the stylus, inoculates a portion of the original sample on the at least one substrate contained in the at least one Petri dish by distributing the portion of the original sample in a line on the at least one substrate contained in the at least one Petri dish through the stylus, with the stylus moved to the cleaning tank, cleans and disinfects the stylus by distributing through the stylus disinfecting product from the storage area for the disinfecting product upstream of the stylus, dilutes a portion of the sample by mixing the portion of the sample with diluent in a first dilution tank to create at least a first sub-sample, takes at least a portion of the at least a first sub-sample from the at least one dilution tank, and inoculates at least a portion of the at least a first sub-sample on the at least one substrate contained in the at least one Petri dish by distributing the at least a portion of the at least a first sub-sample in a line on the at least one substrate contained in the at least one Petri dish through the stylus separate from the original sample.

2. The automatic device of claim 1 wherein the automatic device automatically creates a second sub-sample by taking at least a portion of the first sub-sample from the first dilution tank and diluting at least a portion of the first sub-sample in a second dilution tank by mixing the portion of the first sub-sample with diluents in the second dilution tank and wherein the automatic device automatically inoculates at least a portion of the second sub-sample on the at least one substrate whereby the automatic device automatically dilutes the original sample in at least two successive dilutions to produce the first and second sub-samples and automatically inoculates the first and second sub-samples on the at least one substrate.

3. The automatic device of claim 1 further comprising a measuring device for measuring the sample and the at least one sub-sample.

4. The automatic device of claim 1 wherein there are at least first and second dilution tanks for mixing the original sample with diluents to produce at least first and second sub-samples.

5. An inoculating method using the automatic device of claim 1, the inoculating method comprising:

mixing and collecting the sample from the at least one tank by use of the stylus;

distributing a portion of the sample on the substrate;

depositing a portion of the sample in the at least one dilution tank to obtain a sub-sample;

cleaning and disinfecting the stylus;

mixing and collecting the sub-sample from the at least one dilution tank by use of the stylus; and, distributing a portion of the sub-sample on the substrate.

6. The inoculating method of claim 5 wherein the steps of distributing a portion of the sample and the sub-sample on the substrate comprise distributing a portion of the sample in at least one line on the substrate and distributing a portion of the sub-sample each of the sample in at least one line on the substrate.

7. The inoculating method of claim 6 wherein the sample and the sub-sample are distributed on the substrate in at least double lines.

8. The inoculating method of claim 5 wherein the automatic device further comprises a second dilution tank and further comprising the steps of depositing a portion of the sub-sample in the second dilution tank to obtain a second sub-sample, cleaning and disinfecting the stylus, mixing and collecting the second sub-sample, and distributing a portion of the second sub-sample on the substrate.

9. The inoculating method of claim 5 wherein the steps of collecting the sample, mixing the sample, cleaning the stylus, and distributing the sample and the sub-sample are automatically executed by the automatic device.

10. The inoculating method of claim 9 wherein a dilution rate of the sub-sample is programmable.

11. The automatic device of claim 1 further comprising at least one Petri dish supported by the platform and at least one substrate in the at least one Petri dish.

12. The automatic device of claim 1 wherein the automatic device automatically inoculates a portion of the original sample on the at least one substrate along at least one substantially straight line and wherein the automatic device automatically inoculates at least a portion of the at least a first sub-sample on the at least one substrate along at least one substantially straight line separate from the at least one substantially straight line along which the original sample is inoculated.

13. The automatic device of claim 12 wherein the automatic device automatically distributes a portion of the original sample on the at least one substrate along a substantially straight double line and wherein the automatic device automatically distributes at least a portion of the at least a first sub-sample on the at least one substrate along a substantially straight double line separate from the double line along which the original sample is distributed.

14. The automatic device of claim 12 wherein the at least one substantially straight line along which the original sample is distributed and the at least one substantially straight line of the at least a first sub-sample are drawn at approximately equal linear speeds.

15. The automatic device of claim 14 wherein the at least one substantially straight line along which the original sample is distributed and the at least one substantially straight line of the at least a first sub-sample are drawn at approximately equal distribution rates by programmed operation of the pump and the stylus.

16. The automatic device of claim 1 further comprising an agitator operative to mix samples in the at least one dilution tank wherein the automatic device automatically operates the agitator to mix samples in the at least one dilution tank.

17. The automatic device of claim 1 wherein the automatic device automatically takes at least a portion of the original sample from the least one storage area for the original sample through the stylus, inoculates the portion of the original sample on the at least one substrate contained in the at least one Petri dish by distributing the portion of the original sample in a line on the at least one substrate contained in the at least one Petri dish through the stylus, with the stylus disposed in proximity to the cleaning tank, disinfects the stylus with disinfecting product from the storage area for the disinfecting product upstream of the stylus, dilutes the portion of the sample by mixing the portion of the sample with diluent in the first dilution tank to create at least the first sub-sample, takes at least the portion of the at least a first sub-sample from the at least one dilution tank, and inoculates at least the portion of the at least the first sub-sample on the at least one substrate contained in the at least one Petri dish by distributing the at least a portion of the at least a first sub-sample in the line on the at least one substrate contained in the at least one Petri dish through the stylus separate from the original sample in order.

18. An automatic device for inoculating an original sample on at least one substrate contained in at least one Petri dish, the automatic device comprising:
    a cleaning tank;
    a sample tank for retaining the original sample;
    at least one dilution tank;
    a stylus comprising a tube adapted to take the original sample from the sample tank, to dilute a portion of the sample with diluent in the at least one dilution tank to create at least a first sub-sample, to take at least a portion of the first sub-sample, and to distribute the at least a portion of the first sub-sample on the at least one substrate contained in the at least one Petri dish;
    a platform that retains the sample tank, the cleaning tank, the at least one dilution tank, and the at least one substrate contained in the at least one Petri dish;
    a head wherein the head is movable horizontally relative to the platform, wherein the head is movable vertically relative to the platform, and wherein the head retains the stylus;
    a storage area for diluent disposed upstream of the stylus for supplying diluent to the stylus;
    a storage area for disinfecting product disposed upstream of the stylus for supplying disinfecting product to the stylus; and
    a pump connected to the tube of the stylus to permit taking and distribution of liquids from the sample tank, the at least one dilution tank, and the storage areas for diluent and the disinfecting products;
    wherein, by programmed operation of the head and the pump, the automatic device automatically takes at least a portion of the original sample from the sample tank through the stylus, inoculates a portion of the original sample on the at least one substrate contained in the at least one Petri dish by distributing the portion of the original sample in a line on the at least one substrate contained in the at least one Petri dish through the stylus, with the stylus moved to the cleaning tank, cleans and disinfects the stylus by distributing through the stylus disinfecting product from the storage area for the disinfecting product upstream of the stylus, dilutes a portion of the sample by mixing the portion of the sample with diluent in a first dilution tank to create at least a first sub-sample, takes at least a portion of the at least a first sub-sample from the at least one dilution tank, and inoculates at least a portion of the at least a first sub-sample on the at least one substrate contained in the at least one Petri dish by distributing the at least a portion of the at least a first sub-sample in a line on the at least one substrate contained in the at least one Petri dish through the stylus.

19. The automatic device of claim 18 wherein, by programmed operation of the head and the pump, the automatic device inoculates a portion of the original sample on the at least one substrate contained in the at least one Petri dish by distributing the portion of the original sample in a line on the at least one substrate contained in the at least one Petri dish through the stylus separate from the line of the first sub-sample.

20. The automatic device of claim 18 wherein, by programmed operation of the head and the pump, the automatic device automatically moves the stylus to the cleaning tank and cleans and disinfects the stylus by distributing through the stylus disinfecting product from the storage area for the disinfecting product upstream of the stylus.

* * * * *